(12) United States Patent
Savonnet et al.

(10) Patent No.: US 8,586,774 B2
(45) Date of Patent: Nov. 19, 2013

(54) IHM-2 ORGANIC-INORGANIC HYBRID MATERIAL AND PROCESSES FOR PREPARATION

(75) Inventors: Marie Savonnet, Lyons (FR); David Farrusseng, Belmont D'Azegues (FR); Catherine Pinel, Lyons (FR); Delphine Bazer-Bachi, Irigny (FR); Nicolas Bats, Saint Symphorien D'Ozon (FR); Vincent Lecocq, Orlienas (FR)

(73) Assignees: CNRS, Paris Cedex (FR); IFP Energies nouvelles, Ruiel-Malmaison Cedex (FR)

( * ) Notice: Subject to any disclaimer, the term of this patent is extended or adjusted under 35 U.S.C. 154(b) by 0 days.

(21) Appl. No.: 13/503,460

(22) PCT Filed: Oct. 6, 2010

(86) PCT No.: PCT/FR2010/000673
§ 371 (c)(1), (2), (4) Date: Jul. 16, 2012

(87) PCT Pub. No.: WO2011/048284
PCT Pub. Date: Apr. 28, 2011

(65) Prior Publication Data
US 2012/0277454 A1    Nov. 1, 2012

(30) Foreign Application Priority Data

Oct. 23, 2009 (FR) .................................. 09 05101

(51) Int. Cl.
*C07F 5/00* (2006.01)
*B01J 31/00* (2006.01)

(52) U.S. Cl.
USPC ............................................................ 556/1

(58) Field of Classification Search
USPC ............................................... 556/1; 502/150
See application file for complete search history.

(56) References Cited

U.S. PATENT DOCUMENTS

| 7,202,385 | B2 * | 4/2007 | Mueller et al. | 568/679 |
| 2005/0004404 | A1 | 1/2005 | Muller et al. | |
| 2006/0154807 | A1 * | 7/2006 | Yaghi et al. | 502/150 |
| 2008/0121105 | A1 | 5/2008 | Schubert et al. | |
| 2012/0129684 | A1 * | 5/2012 | Vimont et al. | 502/170 |
| 2012/0283456 | A1 * | 11/2012 | Savonnet et al. | 552/4 |

FOREIGN PATENT DOCUMENTS

| EP | 1 785 428 A1 | 5/2007 |
| WO | WO 2008/061958 A1 | 5/2008 |

OTHER PUBLICATIONS

International Search Report of PCT/FR2010/000673 (Jan. 14, 2011).
C. Volkringer et al., "The Kagome Topology of the Gallium and Indium Metal-Organic Framework Types with a MIL-68 Structure: Synthesis, XRD, Solid-State NMR Characterizations, and Hydrogen Adsorption", Inorganic Chemistry, vol. 47, No. 24 (2008) pp. 11892-11901.

* cited by examiner

*Primary Examiner* — Porfirio Nazario Gonzalez
(74) *Attorney, Agent, or Firm* — Millen, White, Zelano & Branigan, P.C.

(57) ABSTRACT

A new crystallized hybrid material with an organic-inorganic matrix, called IHM-2, containing an inorganic network of metal centers based on the element indium that are connected to one another by organic ligands that are formed by the entity 2-aminoterephthalate $-O_2C-C_6H_3-N_2-CO_2-$ is described. Said material has an X-ray diffraction diagram as given below.

16 Claims, 1 Drawing Sheet

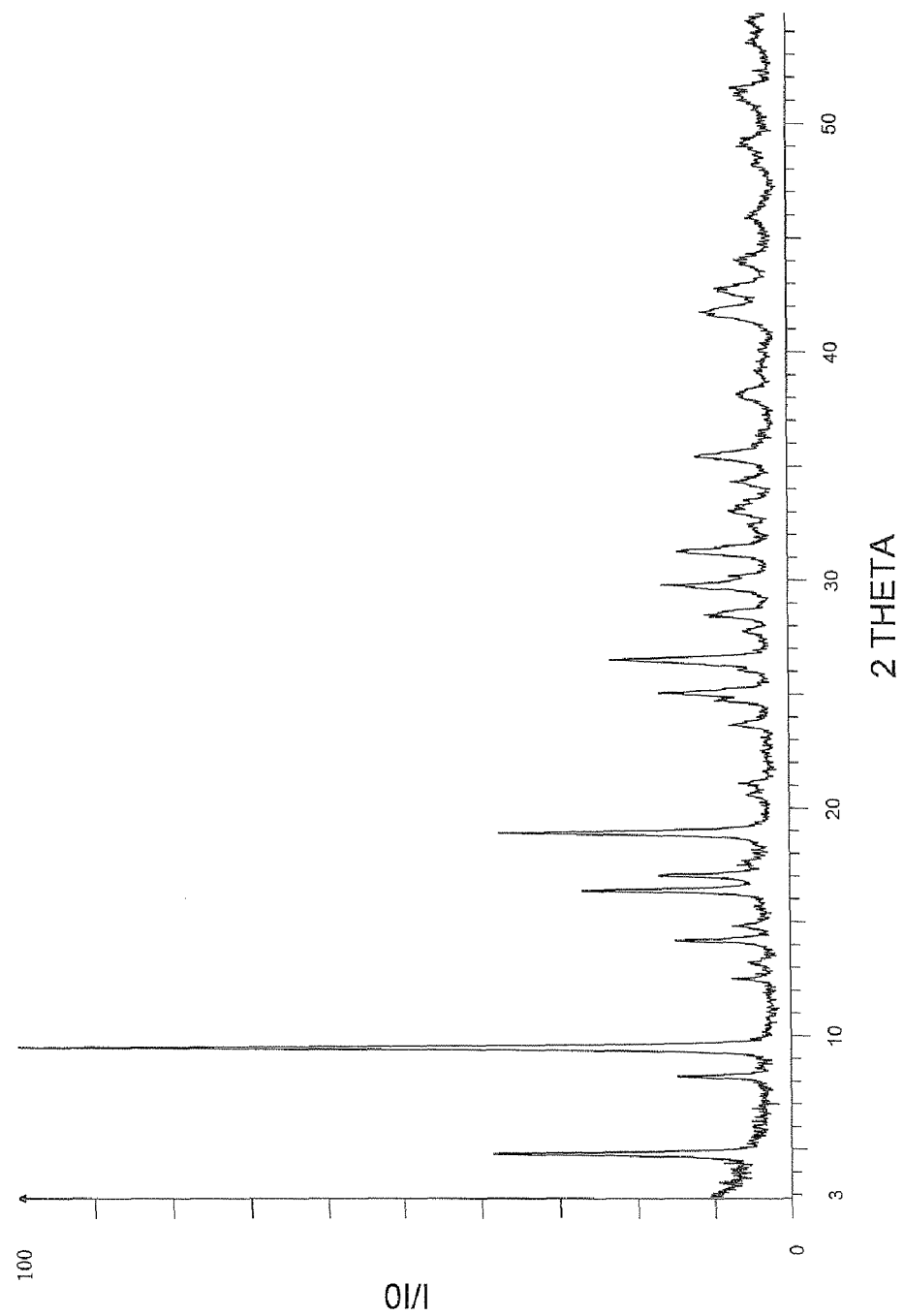

IHM-2 ORGANIC-INORGANIC HYBRID MATERIAL AND PROCESSES FOR PREPARATION

TECHNICAL FIELD OF THE INVENTION

This invention relates to a new crystallized hybrid material with an organic-inorganic mixed matrix, called IHM-2 below, the preparation of said material, as well as its use as catalyst or adsorbent.

PRIOR ART

The family of porous solids, with an undeniable importance as much in applications of daily life as in industrial applications, still arouses major interest in research work carried out in the field of materials.

The inorganic porous solids have been studied extensively so as to increase the opening of their structures so as to facilitate the access of the reagents to the active site or the departure of products from this active site.

Since the 1990's, there has been particular interest in hybrid compounds with an organic-inorganic mixed matrix, thus carrying the number of groups that distinguish the types of porous materials at 3: inorganic materials, carbon-containing materials, and hybrid materials, also called coordination polymers.

These coordination polymers, of which the first were described in the 1960's, are the object of a growing number of publications. Actually, the effervescence around these materials made it possible to attain an already advanced structural diversity in little time (Férey, G., l'actuanté chimique [Chemical Issues], January 2007, No. 304). Conceptually, the porous hybrid solids with an organic-inorganic mixed matrix are quite similar to porous solids with an inorganic skeleton. Like the latter, they combine chemical entities by giving rise to a porosity. The primary difference resides in the nature of these entities. This difference is particularly advantageous and is at the origin of the entire versatility of this category of hybrid solids. Actually, the size of the pores becomes, by using organic ligands, adjustable by means of the length of the carbon-containing chain. The framework, which in the case of inorganic porous materials can accept only some elements (Si, Al, Ge, Ga, and optionally Zn), can, in this case, use all of the cations (except for the alkalines). For these materials, no specific structuring agent is required; the solvent provides this effect by itself.

It therefore clearly appears that this class of materials makes possible a multiplicity of structures and consequently solids that are finely adapted to the applications for which they are designed.

The coordination polymers comprise at least two elements that are called connectors and ligands whose orientation and number of connecting sites are decisive in the structure of the hybrid material. From the diversity of these ligands and connectors, an immense variety of hybrid materials is born, as has already been specified.

Ligand is defined as the organic part of the hybrid material. These ligands are most often di- or tricarboxylates or derivatives of pyridine. Some commonly encountered organic ligands are shown below: bdc=benzene-1,4-dicarboxylate, btc=benzene-1,3,5-tricarboxylate, ndc=naphthalene-2,6-dicarboxylate, bpy=4,4'-bipyridine, hfipbb=4,4'-(hexafluoroisopropylidene)-bisbenzoate, cyclam=1,4,8,11-tetraazacyclotetradecane.

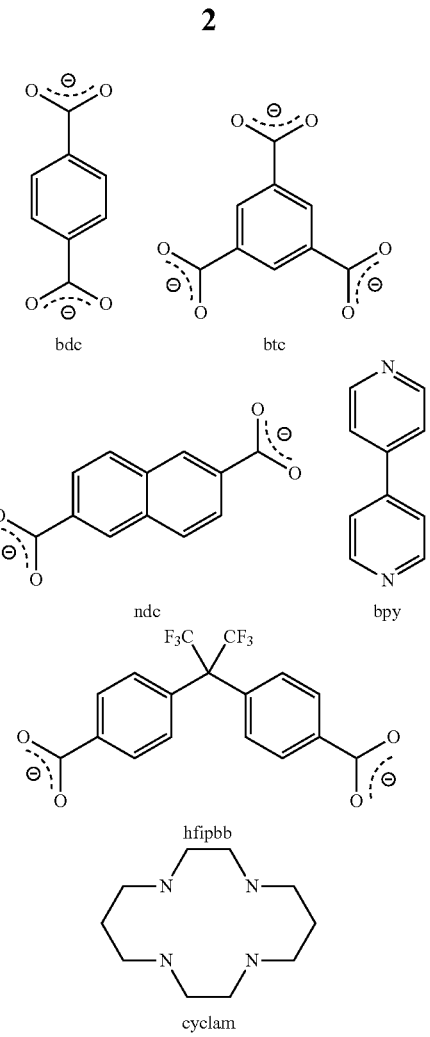

Connector is defined as the inorganic entity of the hybrid material. It may be a cation by itself, a dimer, a trimer, or a tetramer, or else a chain or a plane.

The teams of Yaghi and Férey have thus described a large number of new hybrid materials (series of MOF—"Metal Organic Framework"—and series of MIL—"Materiaux de l'Institut Lavoisier [Lavoisier Institute Materials]," respectively). Numerous other teams have followed this path, and today, the number of new hybrid materials described is expanding rapidly. Most often, the purpose of the studies is to develop ordered structures, having extremely large pore volumes, good thermal stability, and adjustable chemical functionalities.

For example, Yaghi et al. describe a series of boron-based structures in the patent application US 2006/0154807 and indicate their interest in the field of gas storage. The U.S. Pat. No. 7,202,385 discloses a particularly complete summary of the structures that are described in the literature and perfectly illustrates the multitude of materials already existing today.

T. Loiseau et al. (*Inorganic Chemistry.* 2008, 47, 11892-11901) describes an MIL-68 phase based on indium atoms or gallium atoms and BDC (benzene-1,4-dicarboxylate)-type ligands. This compound has a three-dimensional structure in which the one-dimensional inorganic chains with an —In—O(H)— or —Ga—O(H)— pattern are linked to one another by deprotonated terephthalic ligands (BDC=$O_2C$—$C_6H_4$—$CO_2$). Each gallium or indium atom is hexa-coordinated, with two oxygen atoms of the hydroxyl groups being located in apical position and four oxygen atoms that are obtained from four terephthalic ligands being located in equatorial position. In addition, an organic ligand is connected to two indium or gallium atoms (a pair of close atoms of indium or gallium).

DESCRIPTION OF THE INVENTION

This invention has as its object a new crystallized hybrid solid with an organic-inorganic matrix, called IHM-2, containing an inorganic network of metal centers that are based on the element indium and that are connected to one another by organic ligands that are formed by the entity 2-aminoterephthalate $O_2C—C_6H_3—NH_2—CO_2—$. Said IHM-2 material presents a crystalline structure that is isostructural to that of the MIL-68 materials that are known and described above.

The IHM-2 crystallized hybrid material according to the invention has an X-ray diffraction diagram that includes at least the lines that are recorded in Table 1. This diffraction diagram is obtained by radiocrystallographic analysis by means of a Bruker D5005 diffractometer, which is equipped with a graphite curved rear monochromator and a scintillation detector, by using the conventional method of powders with the Kα1 radiation of copper (λ=1.5406 Å). Starting from the position of diffraction peaks shown by the angle 2θ, the reticular equidistances $d_{hkl}$ that are characteristic of the sample are calculated by applying Bragg's equation. The measuring error $\Delta(d_{hkl})$ to $d_{hkl}$ is calculated using Bragg's equation based on the absolute error $\Delta(2\theta)$ that is assigned to the measurement of 2θ. An absolute error of $\Delta(2\theta)$ that is equal to ±0.02° is commonly allowed. The relative intensity $I/I_o$ assigned to each value of $d_{hkl}$ is measured according to the height of the corresponding diffraction peak. The X-ray diffraction diagram of the IHM-2 crystallized hybrid material according to the invention comprises at least the lines with given values of $d_{hkl}$ in Table 1. In the column of $d_{hkl}$, the mean values for the interrecticular distances are indicated in angstroms (Å). Each of these values is to be assigned the measuring error $\Delta(d_{hkl})$ of between ±0.3 Å and ±0.01 Å.

TABLE 1

Mean Values for $d_{hkl}$ and Relative Intensities Measured on an X-Ray Diffraction Diagram of the IHM-2 Crystallized Hybrid Material.

| 2 Theta (°) | $d_{hkl}$ (Å) | $I/I_o$ |
|---|---|---|
| 4.70 | 18.80 | mf |
| 8.12 | 10.88 | ff |
| 9.37 | 9.43 | FF |
| 12.41 | 7.13 | ff |
| 13.12 | 6.74 | ff |
| 14.10 | 6.28 | ff |
| 14.76 | 6.00 | ff |
| 16.29 | 5.44 | f |
| 16.95 | 5.23 | f |
| 18.83 | 4.71 | mf |
| 20.54 | 4.32 | ff |
| 21.07 | 4.21 | ff |
| 23.61 | 3.76 | ff |
| 24.68 | 3.60 | ff |
| 24.99 | 3.56 | f |
| 26.01 | 3.42 | ff |
| 26.44 | 3.37 | f |
| 27.71 | 3.22 | ff |
| 28.42 | 3.14 | ff |
| 29.73 | 3.00 | f |
| 30.14 | 2.96 | ff |
| 31.23 | 2.86 | ff |
| 32.96 | 2.72 | ff |
| 33.47 | 2.68 | ff |
| 34.29 | 2.61 | ff |

TABLE 1-continued

Mean Values for $d_{hkl}$ and Relative Intensities Measured on an X-Ray Diffraction Diagram of the IHM-2 Crystallized Hybrid Material.

| 2 Theta (°) | $d_{hkl}$ (Å) | $I/I_o$ |
|---|---|---|
| 35.42 | 2.53 | ff |
| 37.99 | 2.37 | ff |
| 41.75 | 2.16 | ff |
| 42.73 | 2.11 | ff |
| 43.98 | 2.06 | ff |
| 49.18 | 1.85 | ff |
| 51.55 | 1.77 | ff |
| 53.58 | 1.71 | ff |
| 54.45 | 1.68 | ff | where
FF = Very High;
F = High;
m = Medium;
mf = Medium Low;
f = Low; and
ff = Very Low.
The relative intensity $I/I_o$ is provided in relation to a relative intensity scale where a value of 100 is assigned to the most intense line of the X-ray diffraction diagram: ff < 15; 15 ≤ f < 30; 30 ≤ mf < 50; 50 ≤ m < 65; 65 ≤ F < 85; and FF ≥ 85.

BRIEF DESCRIPTION OF THE DRAWING

The IHM-2 crystallized hybrid material according to the invention has a crystalline structure with a base or topology that is characterized by its X-diffraction diagram provided by FIG. 1.

The IHM-2 crystallized hybrid material according to the invention thus has a chemical composition that has In(OH) ($—O_2C—C_6H_3—NH_2—CO_2—$) as a base pattern. This pattern is repeated n times, with the value of n depending on the crystallinity of said solid.

Said IHM-2 material has a three-dimensional structure in which the one-dimensional inorganic chains with an —In—O(H)— pattern are linked to one another via the 2-aminoterephthalate ligands ($—O_2C—C_6H_3—NH_2—CO_2—$, denoted $NH_2$—BDC). Each indium atom is hexa-coordinated: each indium atom is surrounded by two oxygen atoms of the hydroxyl groups that are located in apical position and by four oxygen atoms that are obtained from four 2-aminoterephthalate ligands that are located in equatorial position. In addition, each $—O_2C—C_6H_3—NH_2—CO_2—$ ($NH_2$—BDC) organic ligand is connected to two indium atoms.

This invention also has as its object the preparation of said IHM-2 crystallized hybrid material with an organic-inorganic mixed matrix. Two processes for the preparation of said IHM-2 material are described below.

A first process for preparation of said IHM-2 crystallized hybrid material with an organic-inorganic mixed matrix comprises at least the following stages:
  i) The dissolution of at least one indium precursor (In prec) in at least one polar organic solvent,
  ii) The addition of 2-aminoterephthalic acid ($NH_2$—$H_2$—BDC) in solution in at least one polar organic solvent,
  iii) The addition of a base B, in solution in at least one polar organic solvent, in the mixture that is obtained in stage ii),
  iv) The precipitation of the 2-aminoterephthalic acid and said indium precursor with said base,
  v) The filtration and the washing, and
  vi) The drying of the material that is obtained.

In accordance with said stage i) of said first process for preparation according to the invention, said indium precursor (denoted In prec) is selected from among the indium salts (III) such as the chlorides, sulfates, acetates or nitrates of indium.

Very preferably, the indium precursor is indium nitrate $In(NO_3)_3$. Said indium precursor is dissolved in a polar organic solvent or a mixture of polar organic solvents. Said solvent is preferably selected from among dimethylformamide (DMF), dimethyl sulfoxide (DMSO), methanol (MeOH), ethanol (EtOH), water ($H_2O$), and tetrahydrofuran (THF); very preferably, it is DMF. A mixture of polar organic solvents comprises at least two solvents that are selected from this list. For example, said indium precursor is dissolved in a mixture of DMSO/MeOH, DMF/EtOH, and THF/$H_2O$.

In accordance with said stage ii) of said first process for preparation according to the invention, 2-aminoterephthalic acid corresponds to 2-amino-1,4-benzene dicarboxylic acid of formula $HO_2C$—$C_6H_3$—$NH_2$—$CO_2H$ (denoted $NH_2$—$H_2$—BDC). It is a commercially available compound. 2-Aminoterephthalic acid, introduced into the solution that is obtained in said stage i), is present in a polar organic solvent or a mixture of polar organic solvents. Said solvent is preferably selected from among dimethylformamide (DMF), dimethyl sulfoxide (DMSO), methanol (MeOH), ethanol (EtOH), water ($H_2O$), and tetrahydrofuran (THF). A mixture of polar organic solvents comprises at least two solvents that are selected from this list. For example, 2-aminoterephthalic acid is present in a mixture of DMSO/MeOH, DMF/EtOH, and THF/$H_2O$ for its addition into the solution that is obtained in said stage i).

In accordance with said stage iii) of said first process for preparation according to the invention, said base B is preferably selected from among 1,4-diazabicyclo[2.2.2]octane (DABCO), 1,8-diazabicyclo[5.4.0]undec-7-ene (DBU), triethylamine, pyridine, soda and ammonia. Said base, introduced into the solution that is obtained in said stage ii), is present in a polar organic solvent or a mixture of polar organic solvents. Said solvent is preferably selected from among dimethylformamide (DMF), dimethyl sulfoxide (DMSO), methanol (MeOH), ethanol (EtOH), water ($H_2O$), and tetrahydrofuran (THF). A mixture of polar organic solvents S comprises at least two solvents that are selected from this list. For example, said base is present in a mixture of DMSO/MeOH, DMF/EtOH, and THF/$H_2O$ for its addition into the solution that is obtained in said stage ii).

The reaction mixture that is obtained at the end of said stage iii) advantageously has the following molar composition: 1 In prec:1 to 3 $NH_2$—$H_2$—BDC:1.8 to 6 B:40 to 500 S. In a more advantageous manner, the molar composition is the following: 1 In prec:1 to 2 $NH_2$—$H_2$—BDC:2 to 6 B:40 to 500 S. In an even more advantageous manner, the molar composition is as follows: 1 In prec:1 $NH_2$—$H_2$—BDC:2 B:40 to 500 S. The formulation of the molar composition that is given above is expressed in terms of molar equivalents. In this formulation, In prec, $NH_2$—$H_2$—BDC and B respectively refer to the indium precursor, 2-amino-1,4-benzene dicarboxylic acid, and the base. The number of moles of polar solvent(s) S corresponds to the total number of moles of polar solvent(s) present in the reaction mixture following the solubilization of the indium precursor, the 2-aminoterephthalic acid, and the base in at least one polar solvent. The polar solvent that is used for implementing each of the stages i), ii) and iii) of said first process for preparation according to the invention can be identical or different, preferably identical.

In accordance with said stage iv) of said first process for preparation according to the invention, the precipitation stage is implemented at a temperature of between 0° C. and 100° C., preferably between 10° C. and 60° C., and most often at ambient temperature. The duration of said precipitation stage is preferably between 1 and 8 hours, very preferably between 1 and 4 hours.

At the end of said precipitation stage, in accordance with said stage v) of said first process for preparation according to the invention, filtration is carried out in such a way as to recover the IHM-2 crystallized material, followed by a washing stage that is carried out in a polar organic solvent, for example DMF, between 100° C. and 200° C., preferably between 150 and 180° C., for a period that advantageously varies between 12 and 48 hours, most often between 18 and 36 hours. Then, the solid is advantageously impregnated, most often by a Soxhlet extractor with a volatile solvent, preferably with dichloromethane, for a period that varies between 24 and 72 hours, most often 48 hours.

In accordance with said stage vi) of said first process for preparation according to the invention, drying of the solid that is obtained at the end of said stage v) for filtration and washing is initiated. The drying is done at a temperature that is preferably between 40 and 200° C., very preferably between 40° C. and 150° C., and even more preferably between 95° C. and 130° C. The drying period is between 1 and 24 hours, and preferably between 10 and 20 hours. The drying can be done under vacuum or in air, and preferably in air.

The crystallized material that is obtained at the end of said stage vi) of said first process for preparation according to the invention is identified as being IHM-2 crystallized hybrid material according to the invention.

Said IHM-2 crystallized hybrid material with an organic-inorganic mixed matrix can be obtained by means of a second process for preparation that is implemented by solvothermal means.

Said second process for preparation of said IHM-2 crystallized hybrid material with an organic-inorganic mixed matrix comprises at least the following stages:
  a) The dissolution of at least one indium precursor (In prec) in at least one polar organic solvent S,
  b) The addition of 2-aminoterephthalic acid ($NH_2$—$H_2$—BDC) in the solution that is obtained in stage a) for forming a reaction mixture,
  c) The solvothermal treatment of said reaction mixture until said IHM-2 material forms,
  d) The filtration and the washing, and
  e) The drying of the material that is obtained.

In accordance with said stage a) of said second process for preparation according to the invention, said indium precursor is selected from among indium salts (III) such as chlorides, sulfates, acetates or nitrates of indium. Very preferably, the indium precursor is the indium nitrate $In(NO_3)_3$. Said indium precursor is dissolved in a polar organic solvent S or a mixture of polar organic solvents S. Said solvent is preferably selected from among dimethylformamide (DMF), dimethyl sulfoxide (DMSO), methanol (MeOH), ethanol (EtOH), water ($H_2O$), and tetrahydrofuran (THF). A mixture of polar organic solvents comprises at least two solvents that are selected from this list. For example, said indium precursor is dissolved in a mixture of DMSO/MeOH, DMF/EtOH, and THF/$H_2O$.

In accordance with said stage b) of said second process for preparation according to the invention, 2-aminoterephthalic acid corresponds to 2-amino-1,4-benzene dicarboxylic acid of formula $HO_2C$—$C_6H_3$—$NH_2$—$CO_2H$ (denoted $NH_2$—$H_2$—BDC). It is a commercially available compound.

The reaction mixture that is obtained at the end of said stage b) advantageously has the following molar composition: 1 In prec:1 to 2 $NH_2$—$H_2$—BDC:200 to 700 S. The formulation of the molar composition given above is expressed in molar equivalent terms. In this formulation, In prec, $NH_2$—$H_2$—BDC and S respectively refer to the indium precursor, 2-aminoterephthalic acid, and the polar solvent that are used for the implementation of said second process for preparation according to the invention.

In accordance with said stage c) of said second process for preparation according to the invention, the solvothermal treatment stage is carried out at a temperature of between 20 and 200° C., preferably between 100 and 150° C. The reaction mixture that is obtained at the end of said stage b) is subjected to said solvothermal treatment until said IHM-2 crystallized material forms. The duration of said treatment is preferably between 12 and 48 hours. Solvothermal treatment is defined in terms of this invention as a treatment, under autogenous pressure, of the reaction mixture, obtained at the end of said stage b) and containing at least said polar solvent, in an autoclave.

At the end of said stage c), filtration is carried out—in accordance with said stage d) of said second process for preparation according to the invention—in such a way as to recover the IHM-2 crystallized material, followed by a washing stage that is carried out in a polar organic solvent, for example DMF, at a temperature of between 100° C. and 200° C., preferably between 150 and 180° C., for a period that varies between 12 and 48 hours, most often between 18 and 36 hours. Then, the solid is advantageously impregnated, most often by a Soxhlet extractor with a volatile solvent, preferably with dichloromethane, for a period that varies between 24 and 72 hours, most often 48 hours.

In accordance with said stage e) of said second process for preparation according to the invention, drying of the solid that is obtained at the end of said stage d) for filtration and washing is initiated. The drying is done at a temperature that is preferably between 40 and 200° C., very preferably between 40° C. and 150° C., and even more preferably between 95° C. and 130° C. The drying period is between 1 and 24 hours, preferably between 10 and 20 hours. The drying can be done under vacuum or in air, preferably in air.

The crystallized material that is obtained at the end of said stage e) of said second process for preparation according to the invention is identified as being the IHM-2 crystallized hybrid material according to the invention.

This invention also has as its object the use of said IHM-2 crystallized hybrid material as described in this description as adsorbent or as catalyst.

A catalyst that contains said IHM-2 material preferably comes in the form of powder, balls, extrudates or pellets. The shaping can be done by any method that is known to one skilled in the art (U.S. Pat. No. 6,893,564). An adsorbent that contains said IHM-2 material can also come in the form of powder, balls, extrudates or pellets.

For example, for the shaping by pelletizing, in particular pelletizing by piston press, roller press, or with or without binders, is used.

The IHM-2 material powders can undergo granulation with, for example, use of organic or inorganic binders as described in the patent application WO 2006/050898. The use of binders, feedstocks, and peptizing agents also makes possible shaping in the form of extrudates by mixing-extrusion, or in the form of balls by the process of drop coagulation.

The shaping of said IHM-2 material can also be done by impregnation of said material on a preformed substrate according to methods that are well known to one skilled in the art.

All of these types of shaping can be done in the presence or the absence of binder.

The invention is illustrated by the following examples that in no case have a limiting nature.

EXAMPLES

Example 1

Preparation by Precipitation of the IHM-2 Crystallized Hybrid Material with an Organic-Inorganic Mixed Matrix According to the Invention 4.82 ml (3.3 mmol) of an indium nitrate solution (Alfa Aesar, 99.99%) in dimethylformamide (DMF, Aldrich, 99.8%) at a concentration of 0.68 mol/L is placed in a Pyrex receptacle with an inside volume of 100 ml. 10.06 ml (3.3 mmol) of a 2-amino-1,4-benzene dicarboxylic acid solution (Alfa Aesar, 99%) in DMF at a concentration of 0.33 mol/L is added thereto. The mixture is stirred for 5 minutes using a magnetic stirrer. After homogenization, 4.83 ml (6.7 mmol) of a 1,4-diazabicyclo[2.2.2]octane solution (DABCO, Aldrich, 98%) in the DMF at a concentration of 1.38 mol/L is added. The reaction mixture has the following molar composition: 3.3 mmol of indium precursor $In(NO_3)_3$:3.3 mmol of 2-aminoterephthalic acid:6.7 mmol of DABCO: 256 mmol of DMF or in molar equivalent:1 $In(NO_3)_3$:1 $NH_2$—$H_2$—BDC:2 DABCO:77 S. The solution is stirred for 120 minutes at ambient temperature in such a way as to initiate the precipitation of the 2-amino-1,4-benzene dicarboxylic acid and indium nitrate with DABCO. After cooling and filtration, the crystallized solid that is obtained is washed (24 hours) with a hot solution (160° C.) of DMF, and then it is impregnated with dichloromethane for a period of 48 hours. After air-drying at a temperature that is equal to 120° C. for a period of 12 hours, a material in powder form is obtained, and said material is analyzed by X-ray diffraction and identified as consisting of IHM-2 solid crystals that have an X-ray diffraction diagram that includes at least the lines that are recorded in Table 1.

Example 2

Preparation by the Solvothermal Method of the IHM-2 Crystallized Hybrid Material with an Organic-Inorganic Mixed Matrix According to the Invention 0.4616 g (1.2 mmol) of indium nitrate (Alfa Aesar, 99.99%) and 35 ml (455 mmol) of DMF (Aldrich, 99.8%) are placed in a PTFE receptacle with an inside volume of 40 ml. 0.4029 g (2.2 mmol) of 2-amino-1,4-benzene dicarboxylic acid (Alfa Aesar, 99%) is added thereto. The mixture is stirred for 5 minutes using a magnetic stirrer. The reaction mixture has the following molar composition: 1.2 mmol of indium precursor $In(NO_3)_3$:2.2 mmol of 2-aminoterephthalic acid: 455 mmol of DMF or in molar equivalent:1 $In(NO_3)_3$:1.8 $NH_2$—$H_2$—BDC:380 S. The PTFE receptacle is then transferred into an autoclave and then heated without stifling at 120° C. for 24 hours. After cooling and filtration, the crystallized solid that is obtained is washed (24 hours) with a hot solution (160° C.) of DMF and then is impregnated with dichloromethane (48 hours). After air-drying at a temperature that is equal to 100° C. for a period of 12 hours, a material is obtained in powder form that is analyzed by X-ray diffraction and identified as consisting of IHM-2 solid crystals that have an X-ray diffraction diagram that includes at least the lines recorded in Table 1.

Example 3

Preparation by Precipitation of IHM-2 Crystallized Hybrid Material for Different Combinations of Bases and Solvents The synthesis that is described in Example 1 is reproduced several times by varying the base and the solvent, with the other operating conditions remaining identical.

The IHM-2 crystallized hybrid material is thus prepared by using the following as base: 1,8-diazabicyclo[5.4.0]undec-7-ene (DBU), triethylamine ($Et_3N$), 1,4-diazabicyclo[2.2.2]octane (DABCO) and pyridine. The synthesis in the presence of each of these bases is reproduced by varying the polar organic solvent.

In a first series of syntheses, the IHM-2 crystallized hybrid material is prepared in the presence of 1,8-diazabicyclo[5.4.0]undec-7-ene (DBU) as base and a single polar solvent (DMF) or a mixture of polar solvents. Thus, several different syntheses are carried out under the same operating and synthesis conditions (molar composition) as those described in Example 1. The mixtures of polar solvents that are used are: a $THF/H_2O$ mixture, a DMSO/MeOH mixture, a $DMSO/H_2O$ mixture, a DMF/EtOH mixture, and a $DMF/H_2O$ mixture. The polar solvents that are used in each of the syntheses are used instead of the DMF that is used in Example 1.

Each solid that is thus obtained is analyzed by X-ray diffraction and identified as consisting of IHM-2 solid crystals having an X-ray diffraction diagram that includes at least the lines that are recorded in Table 1.

In a second series of syntheses, the IHM-2 crystallized hybrid material is prepared in the presence of triethylamine ($Et_3N$) as base and a single polar solvent (DMF) or a mixture of polar solvents. Several different syntheses are thus carried out under the same operating and synthesis conditions (molar composition) as those described in Example 1. The mixtures of polar solvents that are used are: $THF/H_2O$ mixture, DMSO/MeOH mixture, DMF/EtOH mixture, and $DMF/H_2O$ mixture. The polar solvents that are used in each of the syntheses are used instead of the DMF that is used in Example 1.

Each solid that is thus obtained is analyzed by X-ray diffraction and identified as consisting of IHM-2 solid crystals that have an X-ray diffraction diagram that includes at least the lines that are recorded in Table 1.

In a third series of syntheses, the IHM-2 crystallized hybrid material is prepared in the presence of 1,4-diazabicyclo[2.2.2]octane (DABCO) as a base and a mixture of polar solvents. Thus, several different syntheses are carried out under the same operating and synthesis conditions (molar composition) as those described in Example 1. The mixtures of polar solvents that are used are: a $THF/H_2O$ mixture, a DMSO/MeOH mixture, a $DMSO/H_2O$ mixture, a DMF/EtOH mixture, and a $DMF/H_2O$ mixture. The polar solvents that are used in each of the syntheses are used instead of the DMF that is used in Example 1.

Each solid that is thus obtained is analyzed by X-ray diffraction and identified as consisting of IHM-2 solid crystals that have an X-ray diffraction diagram that includes at least the lines that are recorded in Table 1.

In a fourth series of syntheses, the IHM-2 crystallized hybrid material is prepared in the presence of pyridine as a base and a single polar solvent (DMF) or a mixture of polar solvents. Thus, several different syntheses are carried out under the same operating and synthesis conditions (molar composition) as those described in Example 1. The mixtures of polar solvents that are used are: a $THF/H_2O$ mixture, a DMF/EtOH mixture, and a $DMF/H_2O$ mixture. The polar solvents that are used in each of the syntheses are used instead of the DMF that is used in Example 1.

Each solid that is thus obtained is analyzed by X-ray diffraction and identified as consisting of IHM-2 solid crystals that have an X-ray diffraction diagram that includes at least the lines that are recorded in Table 1.

Example 4

Shaping of the IHM-2 Material for Use as Catalyst

The pelletizing of the IHM-2 crystallized hybrid material that is obtained in Example 1 is carried out using a Korsch-brand press (EKO model). The lower punch that has a hole with a diameter of 3.5 mm makes it possible to shape said material in the form of pellets that are 3.5 mm in diameter.

The IHM-2 material that is obtained in Example 1 in powder form is mixed in advance with 0.25% by weight of graphite. The fill shoe of the press is filled with this mixture, and compacting is initiated with the following parameters: die with 15 mm of depth, depth of penetration of the punch that is greater than or equal to 11 mm, speed of rotation of the rotor that is equal to 25 rpm, dimensions of each pellet: diameter that is equal to 3.5 mm, and thickness that is equal to 4 mm.

A catalyst that consists of the IHM-2 crystallized hybrid material is thus obtained.

The invention claimed is:

1. IHM-2 crystallized hybrid material with an organic-inorganic matrix that contains an inorganic network of metal centers that are based on the element indium and that are connected to one another by organic ligands that are formed by the entity 2-aminoterephthalate-$O_2C$—$C_6H_3$—$NH_2$—$CO_2$—, having an X-ray diffraction diagram that includes at least the lines that are recorded in the table below:

| 2 Theta (°) | $d_{hkl}$ (Å) | $I/I_o$ |
|---|---|---|
| 4.70 | 18.80 | mf |
| 8.12 | 10.88 | ff |
| 9.37 | 9.43 | FF |
| 12.41 | 7.13 | ff |
| 13.12 | 6.74 | ff |
| 14.10 | 6.28 | ff |
| 14.76 | 6.00 | ff |
| 16.29 | 5.44 | f |
| 16.95 | 5.23 | f |
| 18.83 | 4.71 | mf |
| 20.54 | 4.32 | ff |
| 21.07 | 4.21 | ff |
| 23.61 | 3.76 | ff |
| 24.68 | 3.60 | ff |
| 24.99 | 3.56 | f |
| 26.01 | 3.42 | ff |
| 26.44 | 3.37 | f |
| 27.71 | 3.22 | ff |
| 28.42 | 3.14 | ff |
| 29.73 | 3.00 | f |
| 30.14 | 2.96 | ff |
| 31.23 | 2.86 | ff |
| 32.96 | 2.72 | ff |
| 33.47 | 2.68 | ff |
| 34.29 | 2.61 | ff |
| 35.42 | 2.53 | ff |
| 37.99 | 2.37 | ff |
| 41.75 | 2.16 | ff |
| 42.73 | 2.11 | ff |
| 43.98 | 2.06 | ff |
| 49.18 | 1.85 | ff |
| 51.55 | 1.77 | ff |

-continued

| 2 Theta (°) | $d_{hkl}$ (Å) | $I/I_o$ |
|---|---|---|
| 53.58 | 1.71 | ff |
| 54.45 | 1.68 | ff | where
FF = Very High;
F = High;
m = Medium;
mf = Medium Low;
f = Low; and
ff = Very Low.
The intensity $I/I_o$ is provided in relation to a relative intensity scale where a value of 100 is assigned to the most intense line of the X-ray diffraction diagram: ff < 15; 15 ≤ f < 30; 30 ≤ mf < 50; 50 ≤ m < 65; 65 ≤ F < 85; and FF ≥ 85.

2. Crystallized hybrid material according to claim 1, such that each organic ligand —$O_2C$—$C_6H_3$—$NH_2$—$CO_2$— ($NH_2$—BDC) is connected to two indium atoms.

3. Crystallized hybrid material according to claim 1 such that it has a chemical composition that has In(OH)(—$O_2C$—$C_6H_3$—$NH_2$—$CO_2$—) as a base pattern.

4. Crystallized hybrid material according to claim 3, such that each indium atom is surrounded by two oxygen atoms from hydroxyl groups that are located in apical position and four oxygen atoms that are obtained from four 2-aminoterephthalate ligands that are located in equatorial position.

5. Process for the preparation of an IHM-2 crystallized hybrid material with an organic-inorganic matrix according to claim 1 that comprises at least the following stages:
   i) The dissolution of at least one indium precursor (In prec) in at least one polar organic solvent,
   ii) The addition of 2-aminoterephthalic acid ($NH_2$—$H_2$—BDC) in solution in at least one polar organic solvent,
   iii) The addition of a base B, in solution in at least one polar organic solvent, in the mixture that is obtained in stage ii),
   iv) The precipitation of the 2-aminoterephthalic acid and said indium precursor with said base,
   v) The filtration and the washing, and
   vi) The drying of the material that is obtained.

6. Process for preparation according to claim 5, such that said indium precursor that is used in said stage i) is indium nitrate.

7. Process for preparation according to claim 5, such that said base that is employed in said stage iii) is selected from among 1,4-diazabicyclo[2.2.2]octane (DABCO), 1,8-diazabicyclo[5.4.0]undec-7-ene (DBU), triethylamine, pyridine, soda and ammonia.

8. Process for preparation according to claim 5, such that the reaction mixture that is obtained at the end of said stage iii) has the following molar composition: 1 In prec:1 to 3 $NH_2$—$H_2$—BDC:1.8 to 6 B:40 to 500 S, where the number of moles of polar solvent(s) S corresponds to the total number of moles of polar solvent(s) present in the reaction mixture following the solubilization of the indium precursor, the 2-aminoterephthalic acid, and the base in at least one polar solvent.

9. Process for preparation according to claim 5, such that said precipitation stage iv) is carried out at a temperature of between 10 and 60° C.

10. Process for preparation according to claim 5, such that the period of said precipitation stage iv) is between 1 and 8 hours.

11. Process for preparation of an IHM-2 crystallized hybrid material with an organic-inorganic matrix according to claim 1 that comprises at least the following stages:
   a) The dissolution of at least one indium precursor (In prec) in at least one polar organic solvent S,
   b) The addition of 2-aminoterephthalic acid ($NH_2$—$H_2$—BDC) in the solution that is obtained in stage a) for forming a reaction mixture,
   c) The solvothermal treatment of said reaction mixture until said IHM-2 material forms,
   d) The filtration and the washing, and
   e) The drying of the material that is obtained.

12. Process for preparation according to claim 11, such that the reaction mixture that is obtained at the end of said stage b) has the following molar composition:
   1 In prec:1 to 2 $NH_2$—$H_2$—BDC:200 to 700 S.

13. Process for preparation according to claim 11, such that said solvothermal treatment stage is carried out at a temperature of between 20 and 200° C.

14. Process for preparation according to claim 11, such that the period of said solvothermal treatment is between 12 and 48 hours.

15. In a catalytic process, the improvement comprising using as the catalyst the IHM-2 crystallized hybrid material with an organic-inorganic matrix according to claim 1.

16. In an adsorption process, the improvement comprising using as the adsorbent the IHM-2 crystallized hybrid material with an organic-inorganic matrix according to claim 1.

* * * * *

UNITED STATES PATENT AND TRADEMARK OFFICE
CERTIFICATE OF CORRECTION

PATENT NO. : 8,586,774 B2  Page 1 of 1
APPLICATION NO. : 13/503460
DATED : November 19, 2013
INVENTOR(S) : Savonnet et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 25 days.

Signed and Sealed this
Twenty-second Day of September, 2015

Michelle K. Lee
*Director of the United States Patent and Trademark Office*